United States Patent [19]

Peters

[11] 4,341,226
[45] Jul. 27, 1982

[54] TEMPORARY LEAD WITH INSERTION TOOL

[75] Inventor: Peter Peters, Brunssum, Netherlands

[73] Assignee: Medtronic, Inc., Minneapolis, Minn.

[21] Appl. No.: 189,531

[22] Filed: Sep. 22, 1980

[51] Int. Cl.$^3$ ............................................... A61N 1/04
[52] U.S. Cl. .................................. 128/784; 128/419 P
[58] Field of Search ...................... 128/419 P, 784, 785

[56] References Cited

U.S. PATENT DOCUMENTS

| | | | |
|---|---|---|---|
| 3,244,174 | 4/1966 | Wesbey et al. | 128/419 P |
| 3,474,791 | 10/1969 | Bentov | 128/419 P |
| 4,144,889 | 3/1979 | Tyers et al. | 128/419 P |

*Primary Examiner*—William E. Kamm
*Attorney, Agent, or Firm*—John L. Rooney; Joseph F. Breimayer; Carl A. Forest

[57] ABSTRACT

A temporary lead for pacing or monitoring purposes with insertion tool. The temporary lead is thin and lightweight having an electrical connector at a proximal end and an electrode at a distal end. A length of surgical thread is permanently attached to the electrode. A helix is molded into the surgical thread at a short distance from the electrode. A curved needle is permanently attached to the surgical thread. The curved needle is inserted into a first location of the tissue manually or using the disclosed tool which provides insertion at a fixed depth. The curved needle exits the tissue at a second location. The curved needle and surgical thread are pulled from the second location thus bringing the electrode into sufficient contact with the tissue. The helix is elongated under the stress of tension supplied to pull the electrode into position. The excess surgical thread is cut at the second location, removing the tension. The helix tends to return to its initial shape, thereby holding the electrode in position until removal. A straight cutting needle, crimped to the proximal end of the electrical conductor, leaves the body percutaneously prior to closing the wound. Upon applying longitudinal force at the proximal end, the helix is again elongated and the lead is removed. The insertion tool moves the curved needle in a fixed arc relative a surface held against the tissue surface. The fixed arc causes a fixed insertion depth as the curved needle travels from the first location to the second location.

5 Claims, 10 Drawing Figures

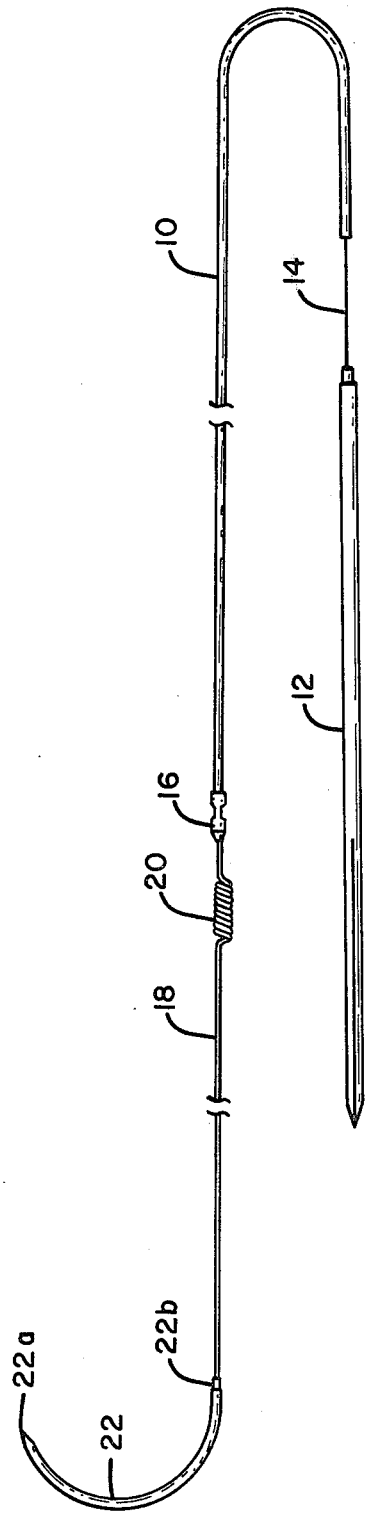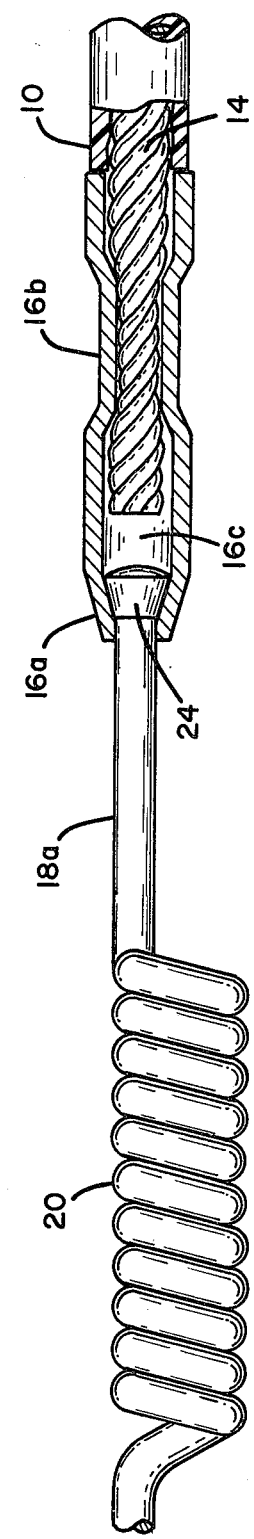

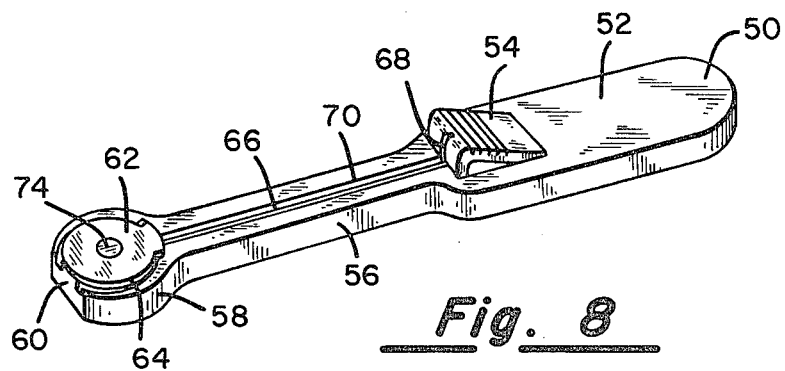
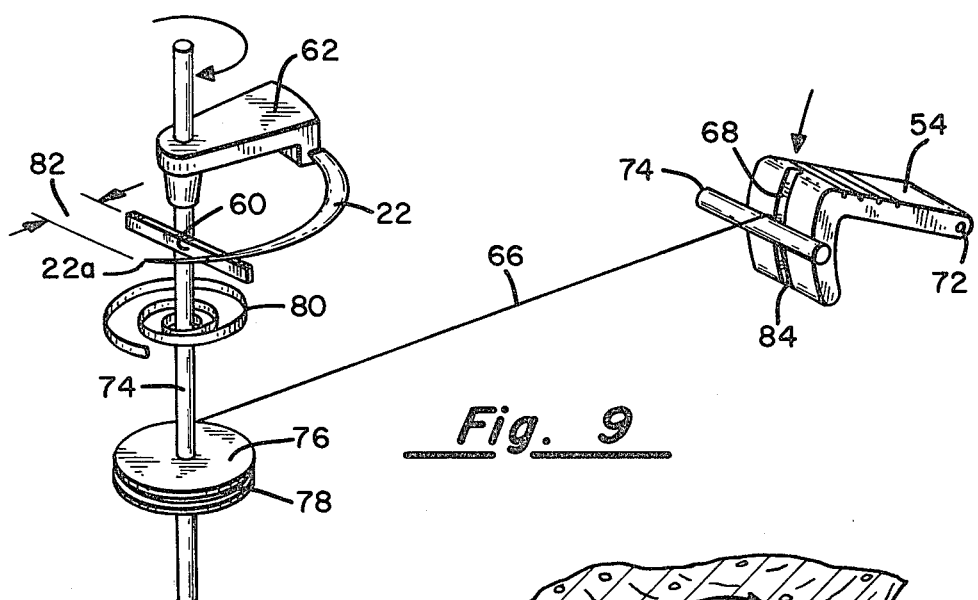
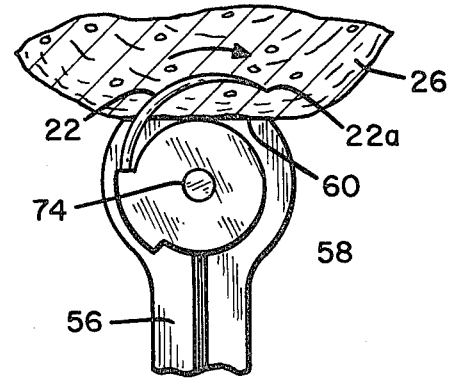

TEMPORARY LEAD WITH INSERTION TOOL

BACKGROUND OF THE INVENTION

1. Field of the Invention

The present invention relates generally to a surgical electrode lead and more specifically relates to a lead for temporary application.

2. Description of the Prior Art

The use of temporary leads for pacing and monitoring purposes is quite common. Specially designed leads are used for such temporary applications which are much lighter and less durable than permanent leads since extended flex life is not required. It is still critical, however, that electrodes be properly affixed to tissue to permit the required transfer of electrical energy. This electrical contact must be established in a manner which permits convenient and safe removal of the lead with minimal permanent scarring and other effects. Furthermore, for expicardial applications, most permanent leads are more costly than is felt justified for temporary use.

Ackerman teaches construction of temporary leads for curing cardiac arrest in U.S. Pat. Nos. 3,485,247 and 3,516,412. The former reference uses a hook-shaped tip for affixing the lead whereas the latter uses resiliency of shape. Neither of these techniques is suitable for most applications, however, as both leads are intended to be percutaneously inserted and actually puncture the myocardium. Because of the permanent effects of this technique, it is not useful under routine circumstances.

The primary method of affixing temporary epicardial leads is with sutures. Typically, this technique provides the greatest reliability with minimal permanent damage. Sutures were used in the earliest pacing applications for affixing all leads. U.S. Pat. No. 3,244,174, issued to Wesbey, et al., teaches a lead whose electrodes are affixed using a suture pad.

U.S. Pat. No. 3,474,791, issued to Benton, teaches a lead having insulation removed at points which permit electrical contact. The lead may have a curved surgical needle attached directly to the distal end of the conductor for sticking the lead directly into the myocardium. Additional sutures are used to further attach the lead to the epicardium.

These earlier suturing techniques for affixing the electrode to the myocardium lend themselves primarily to permanent implantation, since removal of the lead is difficult.

SUMMARY OF THE INVENTION

The present invention is for temporary epicardial stimulation or monitoring. The lead is less expensive than permanent leads, being intended for short-term use only. A single suture affixes the electrode to the epicardium. A length of surgical thread and a curved needle are permanently affixed to the electrode at the distal end of the lead. A helix is molded into the surgical thread a short distance from the electrode.

The curved needle enters and exits the epicardium and the surgical thread is manually pulled until the electrode actually enters the tissue. The helix within the surgical thread is spaced a distance from the electrode ensuring that it is located within the myocardium. The pulling tension on the surgical thread elongates the helix. With tension on the surgical thread, the excess surgical thread is cut at the point of exiting the epicardium. Cutting the surgical thread releases the tension on the helix tending to allow it to return to its original shape. This tendency of the helix holds the electrode in place.

To facilitate proper depth of the stitch, an insertion tool is provided which rotates the curved needle through a fixed arc at a fixed distance relative the epicardial surface. The insertion tool has a shank with a handle at one end and a rotating disc at the other. A pushbutton on the handle causes the disc to rotate a partial turn in one direction. A spring causes the disc to return to its original position. The curved needle is inserted into a slot near the circumference of the disc. The disc end of the insertion tool is held against the epicardium. Pressing of the pushbutton causes insertion of the curved needle to a fixed depth.

After the temporary lead is no longer needed, the lead is removed by pulling on the proximal end. The tension thus created tends to elongate the helix thereby easing removal.

BRIEF DESCRIPTION OF THE DRAWINGS

FIG. 1 is a view of the entire temporary lead.

FIG. 2 is a side sectional view of the electrode with surgical thread and helix attached.

FIG. 8 shows the insertion tool.

FIG. 9 schematically shows the operation of the insertion tool.

FIG. 10 shows insertion of the curved needle using the insertion tool.

DETAILED DESCRIPTION OF THE PREFERRED EMBODIMENTS

Figure 3:
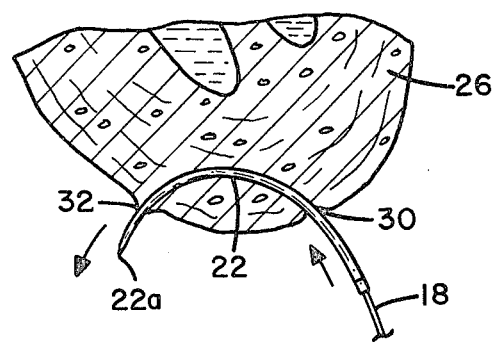
FIG. 3 shows the curved needle as inserted into the myocardium at proper depth.

The present invention is disclosed as embodied in a temporary pacing lead and associated insertion tool. Experiments have indicated that manual insertion of the curved needle is most satisfactory when using the lead for ventricular pacing. The insertion tool is intended for use in the atrial region as the myocardial tissue there is much thinner. However, those of ordinary skill in the art will be readily able to utilize the present invention in other applications and with different dimensions.

FIG. 1 shows the temporary pacing lead. The proximal end contains a metallic, electrically conductive needle 12 which is used as a connector pin to couple the lead to a pulse generator. Needle 12 is attached to the flexible conductor 14 which runs the length of the temporary pacing lead and is attached to electrode 16. Sheath 10 is of a material substantially inert to bodily fluids such as polyethelene. Sheath 10 also electrically insulates conductor 14. A length of surgical thread 18 is permanently attached to electrode 16. Surgical thread 18 has an outside diameter of about 0.35 mm and is a commonly available type such as polypropylene. Helix 20 is molded into the surgical thread by applying hot air to the coiled surgical thread. Curved needle 22 is a standard surgical $-\frac{3}{8}$ circle needle of 12.0 mm radius. The surgical thread is attached to the curved needle by crimp 22b. Needle point 22a is hand honed.

FIG. 2 is a sectional view of electrode 16. The total length of electrode 16 is about 3 mm. The outside diameter of Sheath 10 is approximately 0.7 mm. Sheath 10 extends to the proximal end of electrode 16. Conductor 14 extends distal relative to Sheath 10 and into electrode 16 as shown. Electrode 16 is crimped to securely connect to conductor 14 at indentation 16b. The proximal end of surgical thread 18 is enlarged to produce fastener 24. This may be accomplished by heating the proximal end of surgical thread 18 and applying a force in the distal direction, thus flatening the end.

Fastener 24 is inserted into chamber 16c which lies within electrode 16 between the distal end of conductor 14 and the distal end of electrode 16. The distal end of electrode 16 is swaged producing the conical frustrum 16a, which securely holds fastener 24. Conical frustrum 16a also helps ease insertion of electrode 16 into epicardial tissue.

Between conical frustrum 16a and helix 20 is a length of surgical thread 18a being about 1.0 mm. Helix 20 is about 9-11 turns having an outside diameter of approximately 1.0 mm.

FIG. 3 shows proper insertion of curved needle 22. This may be accomplished manually or through the use of the insertion tool described below. Myocardium 26 is entered at first location 30 and exited at second location 32 by curved needle 22 being moved in the direction shown.

Figure 4:
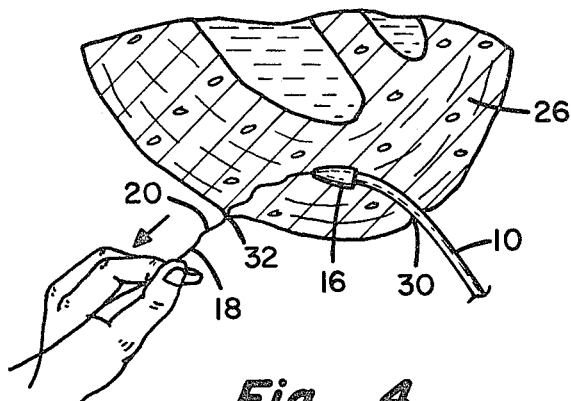
FIG. 4 shows elongation of the helix as the electrode is pulled into position.
Figure 6:
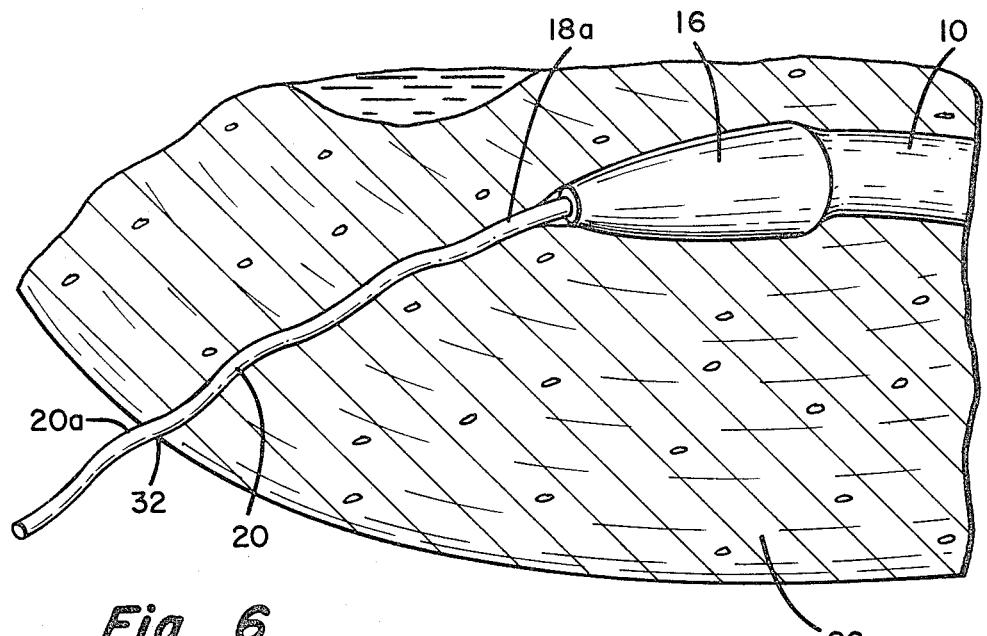
FIG. 6 is a sectional view of the myocardial tissue with tension applied to surgical thread.

FIG. 4 shows the manner in which electrode 16 is properly positioned. Surgical thread 18 is manually pulled from second location 32 until electrode 16 to which it is attached is pulled into the orifice at location 30. Notice that electrode 16 is located completely within myocardial tissue. Because of the stress on helix 20 caused by pulling surgical thread 18 in the direction shown and the friction between electrode 16 and the myocardial tissue, helix 20 becomes temporarily elongated as shown. FIG. 6 shows an enlarged sectional view of myocardial tissue 26 with electrode 16 properly positioned. Notice that a portion of elongated helix 20 extends from the orifice at second location 32.

Figure 5:
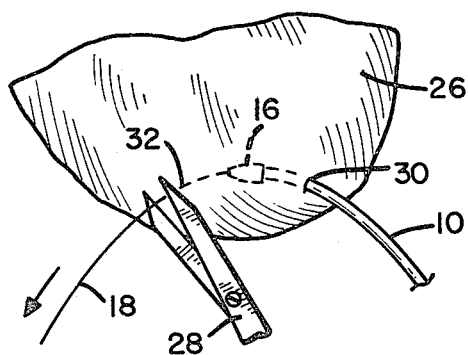
FIG. 5 shows cutting off excess surgical thread.
Figure 7:
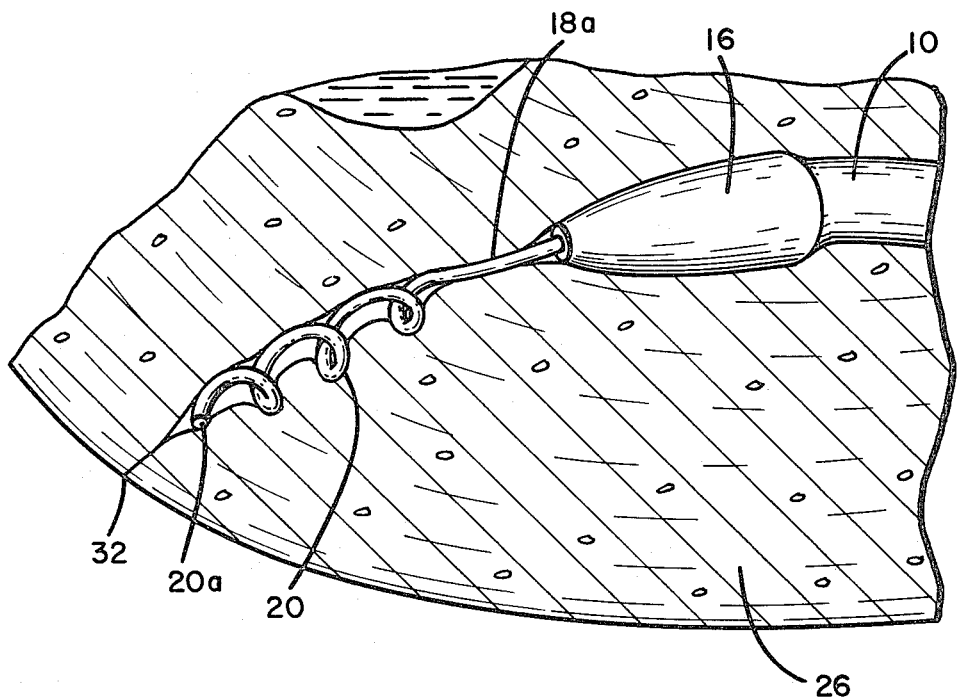
FIG. 7 is a sectional view of the myocardial tissue with tension removed.

FIG. 5 shows removal of the excess surgical thread. While tension is continuously supplied to surgical thread 18 maintaining helix 20 in its elongated state, surgical thread 18 is severed by cutting instrument 28 near second location 32. FIG. 7 is an enlarged sectional view of myocardial tissue 26 following severing of the excess surgical thread. Notice that whereas helix 20 does not return to its initial shape, its longitudinal distance is somewhat reduced causing the tension with the surrounding myocardial tissue which continues to hold electrode 16 in place. Also notice that helix 20 was severed at point 20a. Severing the surgical thread at helix 20 ensures that point 20a will retreat from second location 32 into the myocardial tissue which permits immediate healing of second location 32.

To remove the temporary pacing lead, tension is applied by pulling the proximal end of the temporary pacing lead. The tension tends to elongate helix 20 easing removal. Notice that healing need occur only at a single orifice (i.e., at first location 30) upon removal as the orifice at second location 32 begins healing immediately.

FIG. 8 shows insertion tool 50. As explained above, the use of insertion tool 50 is optional but has proven useful for atrial pacing. Because the thickness of the myocardium in the atrial region is substantially less than in the ventricular region, obtaining of proper depth without piercing the endocardium is more difficult. Insertion tool 50 ensures a constant insertion depth.

Insertion tool 50 has a handle 52 with a pushbutton 54 which is most conveniently pressed by a thumb. Shank 56 contains slot 70 in which cable 66 is stretched. Cable 66 is attached to pushbutton 54 in such a fashion as to be pulled toward handle 52 as pushbutton 54 is depressed. Tool head 58 contains disc 62 which is rotatably attached to tool head 58 by axle 74. Cable 66 is attached to disc 62 in such fashion that disc 62 tends to rotate in a clockwise direction as cable 66 moves toward handle 52. Surface 60 is placed against the epicardium during insertion. Insertion depth is determined by the distance between surface 60 and axle 74. Curved needle 22 (not shown) is inserted into slot 64 in preparation for insertion.

FIG. 9 is a schematic diagram of the operation of insertion tool 50. As can be seen, pushbutton 54 is pivotally mounted to handle 52 by axle 72. Cable 66 is attached to pushbutton 54 at connection point 84. Fixed member 74 is attached to handle 52 to ensure that depressing pushbutton 54 in the direction shown causes cable 66 to be drawn toward pushbutton 54. Channel 68 in pushbutton 54 prevents cable 66 from binding against fixed member 74.

As pushbutton 54 is depressed and cable 66 is drawn toward pushbutton 54, pulley 76 is caused to rotate in a clockwise direction freeing additional cable 78. Rotation of pulley 76 causes rotation of axle 74 to which it is attached. Disc 62 is shown in cutaway fashion. As axle 74 rotates, disc 62 rotates as shown. Curved needle 22, having been inserted into slot 64, is also rotated to enter the epicardium. Spring 80 tending to cause counterclockwise rotation of axle 74 causes disc 62 to return to its initial position upon release of pushbutton 54. Surface 60 is shown. Distance 82 is the distance between the arc traced by needle point 22a and surface 60. Distance 82 is the constant stitch depth produced by insertion tool 50. This distance is, of course, modifiable by changing the distance between surface 60 and axle 74 or the radius of curved needle 22 and disc 62. At present, 1-2 mm is thought appropriate.

FIG. 10 shows insertion of needle 22 into myocardial tissue 26 using insertion tool 50. Notice that surface 60 is positioned flush with the epicardial surface. As needle 22 is rotated in the direction shown proper insertion is accomplished as seen in FIG. 3.

What is claimed is:

1. A lead for establishing electrical contact between body tissue and a medical device comprising:
   a length of conductor having a proximal end and a distal end;
   a sheath attached to the surface of said length of conductor;
   connector means fixedly attached to said proximal end of said length of conductor for electrically coupling said lead to said medical device;
   an electrode fixedly attached to said distal end of said length of conductors;
   a length of surgical thread having a proximal end and a distal end wherein said proximal end of said length of surgical thread is fixedly attached to said electrode;
   a needle fixedly attached to said distal end of said length of surgical thread; and
   means fixedly attached to said length of surgical thread for frictionally resisting the movement of said surgical thread relative to said body tissue.

2. A lead according to claim 1 wherein said frictionally resisting means is fixedly attached to said length of surgical thread at a distance from said proximal end of said length of surgical thread.

3. A lead according to claim 2 wherein said frictionally resisting means further comprises portion of said length of surgical thread having the general shape of a helix.

4. A lead according to claim 1, 2 or 3 wherein said needle is a curved surgical needle.

5. A temporary pacing lead for providing electrical connection between a pulse generator and epicardial tissue comprising:

a length of flexible conductor having a proximal end and a distal end;

insulating sleeve of material substantially inert-to-body fluids fixedly attached to the outer surface of said length of flexible conductor;

a connector means fixedly attached to said proximal end of said length of flexible conductor for electronically coupling said temporary pacing lead to said pulse generator;

an electrode fixedly attached to said distal end of said length of flexible conductor;

a length of surgical thread having a proximal end fixedly attached to said electrode, having a helix molded into said length of surgical thread at a short distance from said proximal end of said length of surgical thread, and having a distal end; and a curved needle fixedly attached to said distal end of said length of surgical thread.

* * * * *